United States Patent [19]

Grantham

[11] 4,215,145

[45] Jul. 29, 1980

[54] MITICIDAL, FUNGICIDAL, AND OVICIDAL SULFENAMIDES

[75] Inventor: Gary D. Grantham, Wilmington, Del.

[73] Assignee: E. I. Du Pont de Nemours and Company, Wilmington, Del.

[21] Appl. No.: 966,591

[22] Filed: Dec. 5, 1978

[51] Int. Cl.$^2$ ...................... A01N 9/20; C07C 145/02; A01N 9/12
[52] U.S. Cl. .................................. 424/324; 260/551 S
[58] Field of Search ............................... 424/330, 324; 260/551 S

[56] References Cited

FOREIGN PATENT DOCUMENTS 846205  3/1977  Belgium .
846419  3/1977  Belgium .
1455207 11/1976  United Kingdom .

*Primary Examiner*—Allen J. Robinson

[57] ABSTRACT

Sulfenamides, such as 1,1,1-trichloro-N-[2-chloro-5-(trifluoromethyl)phenyl]-N-[2,4-dinitro-6-(trifluoromethyl)phenyl]methanesulfenamide, useful for control of mites, plant diseases and insect eggs.

50 Claims, No Drawings

MITICIDAL, FUNGICIDAL, AND OVICIDAL SULFENAMIDES

BACKGROUND OF THE INVENTION

This invention relates to miticidal, fungicidal and ovicidal sulfenamides.

British Pat. No. 1,455,207 discloses pesticidal diphenylamine derivatives of the formulas:

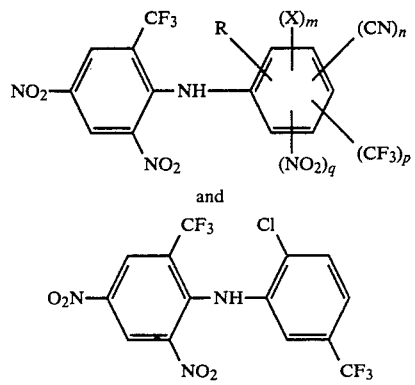

where X and R represent various substituents definitions.

Belgian Pat. No. 846,205 discloses compounds with utility as rodenticides of the formula

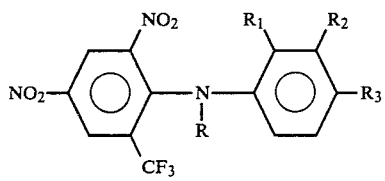

where R, $R_1$, $R_2$ and $R_3$ represent various defined substituents.

Belgian Pat. No. 846,419 discloses compounds with utility as delayed-action rodenticides.

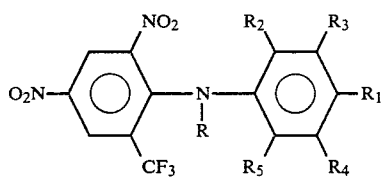

where R, $R_1$, $R_2$, $R_3$, $R_4$ and $R_5$ represent various defined substituents.

SUMMARY OF THE INVENTION

This invention relates to novel sulfenamides of formula (I) to methods for preparing them, and to compositions and methods for using them to control mites, fungus disease of plants and insect eggs.

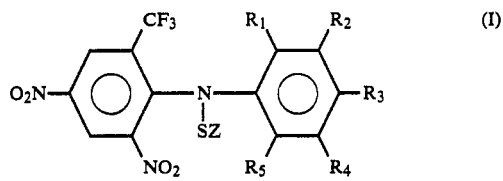

wherein
$R_1$, $R_3$ and $R_4$ independently are H, F, Cl, Br, $NO_2$, $CF_3$, $OCF_3$ or $OCF_2CF_2H$;
$R_2$ is H, F, Cl, Br, $NO_2$ or $CF_3$;
$R_5$ is H or F;
Z is $CCl_3$, $CCl_2F$, $CCl_2CCl_2H$ or $CCl_2CFCl_2$;
provided that when $R_1$ is $NO_2$ or $CF_3$, then $R_3$ must be H or F;
provided that no more than two of the substituents $R_1$, $R_2$, $R_3$ and $R_4$ are simultaneously Cl, Br, $NO_2$, $CF_3$, $OCF_3$ or $OCF_2CF_2H$ and when two $NO_2$ groups are present, they are not ortho to each other.

PREFERRED COMPOUNDS

*Preferred* independently are the following groups of compounds of Formula (I) for reasons of lower cost, lower phytotoxicity, lower mammalian toxicity and/or greater miticidal or fungicidal activity.

Z is $CCl_3$; or
$R_1$ is F, Cl, Br, $CF_3$, $OCF_3$ or $OCF_2CF_2H$; or
$R_2$ is H, F, Cl or Br; or
$R_3$=H, F, Cl or Br; or
$R_4$ is F, Cl, Br, $CF_3$, $OCF_3$ or $OCF_2CF_2H$.

*More preferred* for the preceding reasons are compounds of Formula (I) where
Z is $CCl_3$;
$R_1$ and $R_4$ independently are Cl, $CF_3$, $OCF_3$ or $OCF_2CF_2H$; and
$R_2$, $R_3$ and $R_5$ are H.

*Specifically preferred* for excellent activity, lower phytotoxicity and/or highly favored cost are:
1,1,1-trichloro-N-[2-chloro-5-(trifluoromethyl)-phenyl]-N-[2,4-dinitro-6-(trifluoromethyl)phenyl]-methanesulfenamide
1,1,1-trichloro-N-[2-chloro-5-(trifluoromethoxy)-phenyl]-N-[2,4-dinitro-6-(trifluoromethyl)phenyl]-methanesulfenamide, mixture with the 5-chloro-2-(trifluoromethoxy)phenyl isomer

SYNTHESIS

The compounds of the invention can be prepared by reacting compounds of Formula (II) with sulfenyl chlorides, ClSZ, in the presence of an acid acceptor in an inert solvent as outlined in the following scheme:

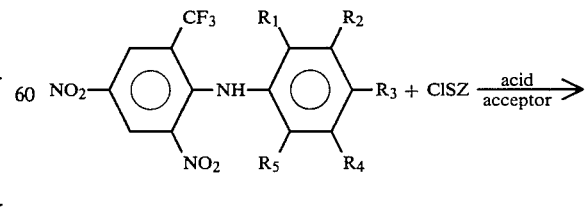

wherein $R_1$, $R_2$, $R_3$, $R_4$ and $R_5$ are as previously defined. Organic bases such as trimethylamine, triethylamine, or pyridine or inorganic bases such as sodium or potassium hydroxide, sodium or potassium carbonate, or sodium hydride may be used as the acid acceptor. Any inert solvent such as toluene, dioxane, tetrahydrofuran, ethyl ether, methylene chloride, etc. may be employed. The reaction is substantially complete at ambient temperature and pressure. Elevated temperature may be used if necessary to shorten reaction time.

The diphenylamines of Formula (II) can be obtained using the procedures described in British Pat. No. 1,455,207.

The following examples further illustrate the preparation of the compounds of this invention. All parts and percentages are by weight, and all temperatures are in degrees centigrade unless otherwise specified.

EXAMPLE 1

Preparation of 1,1,1-trichloro-N-[2-chloro-5-(trifluoromethyl)phenyl]-N-[2,4-dinitro-6-(trifluoromethyl)phenyl]-methanesulfenamide Sodium hydride (0.6 g, 57% mineral oil), washed free of mineral oil with hexane under a nitrogen atmosphere, is slurried in 25 ml of anhydrous tetrahydrofuran and cooled to 0°. A solution of 2-chloro-N-[2,4-dinitro-6-(trifluoromethyl)phenyl]-5-(trifluoromethyl)-benzenamine (4.3 g, 0.010 mole) in 25 ml of anhydrous tetrahydrofuran is then added dropwise with stirring at 0°. When the addition is complete, the solution is allowed to warm to ambient temperature and stirred for one hour. Perchloromethyl mercaptan (1.9 g, 0.010 mole) is then added and stirring is continued for two hours. The reaction mixture is then poured into water, extracted with methylene chloride, dried over anhydrous magnesium sulfate and stripped under vacuum to afford an orange resin. Chromatography on silica gel utilizing 1-chlorobutane/hexane (1:1 by vol) as the eluent affords 3.5 g of 1,1,1-trichloro-N-[2-chloro-5-(trifluoromethyl)phenyl]-N-[2,4-dinitro-6-(trifluoromethyl)phenyl]methanesulfenamide as a yellow oil which crystallizes on standing, m.p. 134°–137°.

Calculated for $C_{15}H_5N_3O_4SF_6Cl_4$: C, 31.11; H, 0.87; N, 7.26. Found: C, 31.4; H, 0.94; N, 7.68.

EXAMPLE 2

Preparation of 1,1,1-trichloro-N-[2-chloro-5-(trifluoromethoxy)phenyl]-N-[2,4-dinitro-6-(trifluoromethyl)phenyl]methanesulfenamide and 1,1,1-trichloro-N-[5-chloro-2-(trifluoromethoxy)phenyl]-N-[2,4-dinitro-6-(trifluoromethyl)phenyl]methanesulfenamide as an approximately 50:50 mixture a. 2-chloro-N-[2,4-dinitro-6-(trifluoromethyl)phenyl]-5-(trifluoromethoxy)benzenamine and 5-chloro-N-[2,4-dinitro-6-(trifluoromethyl)phenyl]-2-(trifluoromethoxy)benzenamine as an approximately 50:50 mixture To a stirred solution of 2.12 g (0.01 mole) of 2-chloro-5-(trifluoromethoxy)benzenamine and 5-chloro-2-(trifluoromethoxy)benzenamine [obtained as an approximately 50:50 mixture utilizing the procedure described in Chem Abstr. 51, 15517 (1957)] in 15 ml of dimethylformamide is added 1.29 g (0.02 mole) of 85% KOH powder. After 15 minutes, this mixture (purple solution plus KOH) is added to a stirred, cooled (ice bath) solution of 2.71 g (0.01 mole) of 2-chloro-3,5-dinitrobenzotrifluoride in 15 ml of dimethylformamide. The mixture is allowed to stir overnight at ambient temperature.

The red mixture is poured into ice water, acidified with conc. hydrochloric acid, and extracted with 1-chlorobutane. The 1-chlorobutane extract is washed with water, twice with 6% potassium carbonate solution (a little solid is filtered off), dried and treated with activated carbon. The filtered solution is evaporated to afford 4.26 g (96%) of 2-chloro-N-[2,4-dinitro-6-(trifluoromethyl)phenyl]-5-(trifluoromethoxy)benzenamine and 5-chloro-N-[2,4-dinitro-6-(trifluoromethyl)phenyl]-2-(trifluoromethoxy)benzenamine (approximately equal amounts) as an orangish-red oil.

b. 1,1,1-trichloro-N-[2-chloro-5-(trifluoromethoxy)phenyl]-N-[2,4-dinitro-6-(trifluoromethyl)phenyl]methanesulfenamide and 1,1,1-trichloro-N-[5-chloro-2-(trifluoromethoxy)phenyl]-N-[2,4-dinitro-6-(trifluoromethyl)phenyl]methanesulfenamide as an approximately 50:50 mixture Sodium hydride (0.6 g, 57% in mineral oil), washed free of mineral oil with hexane under a nitrogen atmosphere, is slurried in 25 ml of anhydrous tetrahydrofuran and cooled to 0°. A solution of the mixture obtained in part a. above (4.5 g, 0.01 mole) in 25 ml of anhydrous tetrahydrofuran is then added dropwise with stirring at 0°. When the addition is complete, the reaction mixture is allowed to warm to ambient temperature and stirred for one hour. Perchloromethyl mercaptan (1.9 g, 0.01 mole) is then added and stirring is continued at ambient temperature for two hours. The reaction mixture is then poured into water, extracted with methylene chloride, dried over anhydrous magnesium sulfate and stripped to afford 5.5 g of a viscous orange resin. Chromatography on silica gel with 1-chlorobutane/hexane (1:1 by volume) as the eluent affords 4.2 g of 1,1,1-trichloro-N-[2-chloro-5-(trifluoromethoxy)phenyl]-N-[2,4-dinitro-6-(trifluoromethyl)phenyl]methanesulfenamide and 1,1,1-trichloro-N-[5-chloro-2-(trifluoromethoxy)phenyl]-N-[2,4-dinitro-6-(trifluoromethyl)phenyl]methanesulfenamide (in approximately equal amounts) as a glassy orange resin.

EXAMPLE 3

Preparation of a mixture of 1,1,1-trichloro-N-[2-chloro-5-(1,1,2,2-tetrafluoroethoxy)phenyl]-N-[2,4-dinitro-6-(trifluoromethyl)phenyl]methanesulfenamide and 1,1,1-trichloro-N-[5-chloro-2-(1,1,2,2-tetrafluoroethoxy)phenyl]-N-[2,4-dinitro-6-(trifluoromethyl)phenyl]methanesulfenamide a. Preparation of N-[5-chloro-2-(1,1,2,2-tetrafluoroethoxy)phenyl]-2,4-dinitro-6-(trifluoromethyl)benzenamine as a mixture with N-[2-chloro-5-(1,1,2,2-tetrafluoroethoxy)phenyl]2,4-dinitro-6-(trifluoromethyl)benzenamine 1. 4-Chlorophenol reacts under basic catalysis with tetrafluoroethylene to give 1-chloro-4-(1,1,2,2-tetrafluoroethoxy)benzene as a colorless oil of b.p. 68° at 12 Torr. [For example, see J. Am Chem. Soc. 73, 5831 (1951) and Chem. Abstr. 73, 36584q.]

2. 1-Chloro-4-(1,1,2,2-tetrafluoroethoxy)benzene is nitrated during 1 hour at 22°–25° with mixed sulfuric/90% nitric acids to provide a mixture of the two mononitro compounds, 1-chloro-2-nitro-4-(1,1,2,2-tetrafluoroethoxy)benzene and 1-chloro-3-nitro-4-(1,1,2,2-tetrafluoroethoxy)-benzene as a yellow oil b.p. 130° at 13 Torr.

3. The mixture of moninitro compounds is reduced with iron in aqueous acetic acid to provide the two isomeric benzenamine derivatives, 5-chloro-2-(1,1,2,2-tetrafluoroethoxy)benzenamine and 2-chloro-5-(1,1,2,2-tetrafluoroethoxy)benzenamine, as an oil of b.p. 115°–117° at 13 Torr.

4. To a stirred, ice-cooled solution of 6.09 g (0.025 mole) of the above mixed benzenamines in 37 ml of dimethylformamide is added 3.30 g of 85% KOH powder. After 20 minutes in the cold, the mixture is treated with a solution of 6.76 g (0.025 mole) of 2-chloro-3,5-dinitrobenzotrifluoride in 37 ml of dimethylformamide. After 20 minutes in the cold, the mixture is allowed to warm to ambient temperature and stirred for 18 hours. The mixture is poured into 300 ml of ice water, acidified with conc. hydrochloric acid, and extracted with 1-chlorobutane. The 1-chlorobutane extracts are washed with water, and 6% potassium carbonate solution (4 times), then dried over anhydrous magnesium sulfate, treated with activated carbon and filtered. The filtrate is stripped under vacuum to afford a mixture of N-[5-chloro-2-(1,1,2,2-tetrafluoroethoxy)phenyl]-2,4-dinitro-6-(trifluoromethyl)benzenamine and N-[2-chloro-5-(1,1,2,2-tetrafluoroethoxy)phenyl]-2,4-dinitro-6-(trifluoromethyl)benzenamine as a red oil.

b. Preparation of a mixture of 1,1,1-trichloro-N-[2-chloro-5-(1,1,2,2-tetrafluoroethoxy)phenyl]-N-[2,4-dinitro-6-(trifluoromethyl)phenyl]methanesulfenamide and 1,1,1-trichloro-N-[5-chloro-2-(1,1,2,2-tetrafluoroethoxy)phenyl]-N-[2,4-dinitro-6-(trifluoromethyl)phenyl]methanesulfenamide Sodium hydride (0.6 g, 57% in mineral oil), washed free of mineral oil with hexane under a nitrogen atmosphere, is slurried in 25 ml of anhydrous tetrahydrofuran and cooled to 0° C. A solution of the mixed benzenamine obtained above (4.8 g 0.01 mole) in 25 ml of anhydrous tetrahydrofuran is then added dropwise with stirring at 0°. After the addition is complete, the reaction mixture is allowed to warm to ambient temperature and stirred for 1 hour. Perchloromethyl mercaptan (3.7 g, 0.02 mole) is added and the mixture stirred for 15 hours. The reaction mixture is then poured into water, extracted with methylene chloride, dried over anhydrous magnesium sulfate and stripped to afford a dark oil. Chromatography on silica gel with 1-chlorobutane/hexane (1:2 by volume) as the eluent affords a mixture of 1,1,1-trichloro-N-[2-chloro-5-(1,1,2,2-tetrafluoroethoxy)phenyl]-N-[2,4-dinitro-6-(trifluoromethyl)phenyl]-methanesulfenamide and 1,1,1-trichloro-N-[5-chloro-2-(1,1,2,2-tetrafluoroethoxy)phenyl]-N-[2,4-dinitro-6-(trifluoromethyl)phenyl]methanesulfenamide as an orange glassy resin.

The procedure described in Examples 1, 2, and 3 above may be used to prepare the compounds of Tables I, II, III, and IV.

TABLE I

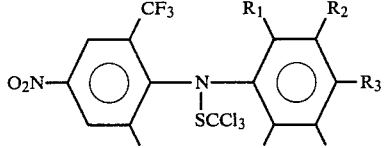

| $R_1$ | $R_2$ | $R_3$ | $R_4$ | $R_5$ | m.p. |
|---|---|---|---|---|---|
| Cl | H | H | $CF_3$ | H | 134°–137° C. |
| Cl | H | H | $OCF_3$ | H | |
| $OCF_3$ | H | H | Cl | H | |
| Cl | H | H | H | H | 153°–155° C. |
| $OCF_3$ | H | H | $OCF_3$ | H | |
| $OCF_3$ | H | $OCF_3$ | H | H | |
| $OCF_2CF_2H$ | H | $OCF_2CF_2H$ | H | H | |
| $OCF_2CF_2H$ | H | H | $OCF_2CF_2H$ | H | |
| Cl | H | H | Cl | H | 166°–168° C. |
| H | $CF_3$ | Cl | H | H | 65°–70° C. |
| H | H | Cl | H | H | |
| F | H | Cl | H | H | |
| Br | H | H | $CF_3$ | H | |
| Br | H | H | $OCF_3$ | H | } 134°–139° C. (for 1 isomer) |
| $OCF_3$ | H | H | Br | H | |
| $NO_2$ | H | H | Cl | H | |
| Cl | H | $NO_2$ | H | H | |
| F | H | F | H | H | |
| H | H | H | H | H | |
| Br | H | Br | H | H | |
| H | Cl | H | H | H | |
| H | Br | H | H | H | |
| H | $NO_2$ | H | H | H | |
| F | H | $CF_3$ | H | H | |
| H | $NO_2$ | Cl | H | H | 164°–166° C. |
| F | H | F | H | F | 130°–133° C. |

TABLE II

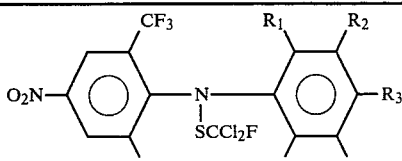

| $R_1$ | $R_2$ | $R_3$ | $R_4$ | $R_5$ |
|---|---|---|---|---|
| Cl | H | H | $CF_3$ | H |
| H | H | H | H | H |
| Br | H | $CF_3$ | H | H |
| $OCF_3$ | H | H | Cl | H |
| Cl | H | H | $OCF_2CF_2H$ | H |
| Cl | H | Cl | H | H |

TABLE III $O_2N\text{-}C_6H_3(CF_3)(NO_2)\text{-}N(SCCl_2CCl_2H)\text{-}C_6H(R_1)(R_2)(R_3)(R_4)(R_5)$

| R₁ | R₂ | R₃ | R₄ | R₅ |
|---|---|---|---|---|
| Cl | H | H | CF₃ | H |
| Cl | H | H | OCF₃ | H |
| H | H | H | H | H |
| Br | H | CF₃ | H | H |
| Cl | H | NO₂ | H | H |
| OCF₂CF₂H | H | H | Cl | H |
| Cl | H | Cl | H | H |

TABLE IV $O_2N\text{-}C_6H_3(CF_3)(NO_2)\text{-}N(SCCl_2CCl_2F)\text{-}C_6H(R_1)(R_2)(R_3)(R_4)(R_5)$

| R₁ | R₂ | R₃ | R₄ | R₅ |
|---|---|---|---|---|
| Cl | H | H | CF₃ | H |
| H | H | H | H | H |
| Br | H | CF₃ | H | H |
| Cl | H | H | OCF₃ | H |
| OCF₂CF₂H | H | H | Cl | H |

FORMULATION

Useful formulations of the compounds of Formula (I) can be prepared in conventional ways. They include dusts, solutions, suspensions, emulsions, wettable powders, emulsifiable concentrates and the like. Many of these may be applied directly. Sprayable formulations can be extended in suitable media and used at spray volumes of from a few pints to several hundred gallons per acre. High-strength compositions are primarily used as intermediates for further formulation. The formulations, broadly, contain about 1% to 99% by weight of active ingredient(s) and at least one of (a) about 0.1% to 20% surfactant(s) and (b) about 1% to 99% solid or liquid diluent(s). More specifically, they will contain these ingredients in the following approximate proportions:

| | Percent by Weight | | |
|---|---|---|---|
| | Active Ingredient | Diluent(s) | Surfactant(s) |
| Wettable Powders | 20–90 | 0–74 | 1–10 |
| Oil Suspensions, Emulsions, Solutions (including Emulsifiable Concentrates) | 5–50 | 40–95 | 0–15 |
| Aqueous Suspensions | 10–50 | 40–84 | 1–20 |
| Dusts | 1–25 | 70–99 | 0–5 |
| Granules and Pellets | 1–95 | 5–99 | 0–15 |
| High-Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd. Edn., Dorland Books, Caldwell, N.J. The more absorptive diluents are preferred for wettable powders and the denser ones for dusts. Typical liquid diluents and solvents are described in Marsden, "Solvents Guide", 2nd. Edn., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Co., Ridgewood, New Jersey, as well as Sisely and Wood, "Encyclopedia of Surface Active Agents", Chemical Publ. Co., Inc., New York, 1964, list surfactants and recommended uses. All formulatiosn can contain minor amounts of additives to reduce foam, caking, corrosion, microbiological growth, promote sticking, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084).

For further information regarding the art of formulation, see for example:

J. B. Buchanan, U.S. Pat. No. 3,576,834, Apr. 27, 1971, Col, 5, Line 36 through Col. 7, Line 70 and Ex. 1–4, 17, 106, 123–140;

R. R. Shaffer, U.S. Pat. No. 3,560,616 Feb. 2, 1971, Col. 3, Line 48 through Col. 7, Line 26 and Examples 3–9, 11–18;

E. Somers, "Formulation", Chapter 6 in Torgeson, "Fungicides", Vol, I, Academic Press, New York, 1967.

EXAMPLE 1

Wettable Powder

| | |
|---|---|
| 1,1,1-Trichloro-N-[2-chloro-5-(trifluoromethoxy)-phenyl]-N-[2,4-dinitro-6-(trifluoromethyl)phenyl]-methanesulfenamide, 50/50 mixture with the 5-chloro-2-(trifluoromethoxy)phenyl isomer | 40% |
| Dioctyl sodium sulfosuccinate | 1.5% |
| Sodium ligninsulfonate | 3% |
| Low-viscosity methyl cellulose | 1.5% |
| Attapulgite | 54% |

The ingredients are thoroughly blended, passed through an air mill, to produce an average particle size under 15 microns, reblended, and sifted through a U.S. Ser. No. 50 sieve (0.3 mm opening) before packaging.

All compounds of the invention may be formulated in the same manner, and dispersed in water for application.

EXAMPLE 2

Wettable Powder

| | |
|---|---|
| 1,1,1-Trichloro-N-[2-chloro-5-(trifluoromethyl)-phenyl]-N-[2,4-dinitro-6-(trifluoromethyl)-phenyl]methanesulfenamide | 80% |
| Sodium alkylnaphthalenesulfonate | 2% |
| Sodium ligninsulfonate | 2% |
| Synthetic amorphous silica | 3% |

| -continued | |
|---|---|
| Kaolinite | 13% |

The ingredients are combined in an efficient blender, passed through a hammer mill to produce particles below 40 microns, and then reblended. The product is sifted through a U.S.S. No. 50 sieve (0.3 mm openings) before packaging.

EXAMPLE 3

Dust

| Wettable powder of Example 1 | 10% |
|---|---|
| Pyrophyllite (powder) | 90% |

The wettable powder and the pyrophyllite diluent are thoroughly blended and then packaged. The product is suitable for use as a dust.

EXAMPLE 4

Aqueous Suspension

| 1,1,1-trichloro-N-[2-chloro-5-(trifluoromethyl)-phenyl]-N-[2,4-dinitro-6-(trifluoromethyl)-phenyl]methanesulfenamide | 25% |
|---|---|
| Hydrated attapulgite | 3% |
| Crude calcium ligninsulfonate | 10% |
| Sodium dihydrogen phosphate | 0.5% |
| Water | 61.5% |

The ingredients are ground together in a sand mill until the solid particles have been reduced to diameters under 10 microns. The product may be diluted with water for spray application.

EXAMPLE 5

Dust Seed Coat

| 1,1,1-Trichloro-N-[2-chloro-5-(trifluoromethyl)-phenyl]-N-[2,4-dinitro-6-(trifluoromethyl)-phenyl]methanesulfenamide | 75% |
|---|---|
| Permanent Red 2 B, Calcium Salt, | 5% |
| Diatomaceous Earth | 20% |

The ingredients are blended, coarsely hammer-milled and passed through an air mill to product particles of active ingredient that are all below 10 microns in diameter. The product is reblended before packaging.

EXAMPLE 6

Slurry Seed Coat

| 1,1,1-Trichloro-N-[2-chloro-5-(trifluoromethoxy)-phenyl]-N-[2,4-dinitro-6-(trifluoromethyl)-phenyl]methanesulfenamide, 50/50 mixture with the 5-chloro-2-(trifluoromethoxy)phenyl isomer | 50% |
|---|---|
| Calcium ligninsulfonate | 4% |
| Trimethyl nonyl polyethylene glycol ether | 4% |
| Rhodamine B | 1% |
| Permanent Red 2 B, calcium salt, extended on Blanc Fixe | 1% |
| Diatomaceous earth | 40% |

The liquid surfactant is sprayed on the diatomaceous earth, the other ingredients are then added thoroughly mixed together in an efficient blender. The mixture is then coarsely hammermilled and passed through an air mill to produce particles of active ingredient that are less than 10 microns in diameter. The product is reblended before packaging. The product may be extended in water and applied to seed in a commercial seed treater.

USE

The compounds (I) of this invention show a high degree of pesticidal activity combined with substantially reduced phytotoxicity relative to the benzenamines (II) active against a similar range of pests. Many of the compounds (I) are also substantially less toxic to mammals (e.g. as eye injurants) than the corresponding benzenamines (II).

The compounds of this invention are useful as miticides and can be used to protect plants from damage caused by these pests. More specifically, fruits, field crops, vegetables and ornamentals can be protected.

When mites come into contact with the compounds of this invention, either in the form of direct sprays or by walking over surfaces which have been treated, they are killed if they have been exposed to a sufficiently high dosage. While most plants are able to tolerate the presence of very small numbers of mites without apparent adverse effect, the reproductive capacity of these pests is enormous. Generally, mite populations rapidly build up, easily out-stripping parasite and predator capabilities for control. Growers noting rapid mite build-up must take immediate action to prevent damage to economically important crops. Thus, a method is needed for immediately reducing mite build-up and thereby preventing damage to important crops.

The method of this invention, namely, contact mites with a miticidally effective concentration, is a most desirable method for control of these pests. For instance, very small quantities of compounds are required for miticidal activity.

The quantity of compound needed for miticidal activity will vary depending on the specific situation. Among the variables that must be considered in deciding on the quantity of chemical to be used are the specific compound itself, the specific mite to be controlled, weather conditions, the type of crop, the stage of development of the crop, the volume of spray applied population pressure, and the interval between applications. For plant protection, solutions or suspensions containing as little as 2.5 ppm of active ingredient in a spray solution may prove effective under a given set of circumstances. For field usage, however, in high-volume applications, aqueous spray preparations containing 5–2500 ppm of active ingredient are generally useful. Preferred are suspensions containing 20–500 ppm, and most preferred are those containing 80–320 ppm. On an area basis, in general, 0.03 to 5.5 kilograms of active-ingredient per hectare are acceptable, preferably 0.03 to 3 kilograms, and most preferable 0.06 to 2 kg. When applied in an orchard, spraying is continued until run-off is observed.

It may be desirable or useful to mix the compounds of this invention with other agricultural pesticides or adjuvants. Such mixtures often increase the effectiveness of the application on mites and broaden the scope of control to embrace other pests such as insects, fungi, nematodes, or bacteria. Pesticides with which the compounds of this invention may be mixed to achieve broader-spectrum activity include:
Fungicides:
methyl 2-benzimidazolecarbamate (carbendazim)

tetramethyl thiuram disulfide (thiuram)
n-dodecylguanidine (dodine)
manganese ethylenebisdithiocarbamate (maneb)
1,4-dichloro-2,5-dimethoxybenzene (chloroneb)
methyl 1-(butylcarbamoyl)-2-benzimidazolecarbamate (benomyl)
N-trichloromethylthiotetrahydrophthalimide (captan)
N-trichloromethylthiophthalimide (folpet)
Bactericides:
tribasic copper sulfate
streptomycin sulfate
Acaricides:
senecioic acid, ester with 2-sec-butyl-4,6-dinitrophenol ("Morocide")
6-methyl-1,3-dithiolo[2,3-β]quinoxolin-2-one ("Morestan")
ethyl 4,4'-dichlorobenzilate (Chlorobenzilate ®)
1,1-bis(p-chlorophenyl)-2,2,2-trichloroethanol (Kelthane ®)
bis(pentachloro-2,4-cyclopentadien-1-yl) (Pentac ®)
tricyclohexyltin hydroxide (Plictran ®)
Nematicides:
S-methyl 1-(dimethylcarbamoyl)-N-(methylcarbamoyloxy)thioformimidate (Vydate ®)
S-methyl 1-carbamoyl-N-(methylcarbamoyloxy)thioformimidate
N-isopropylphosphoramidic acid, O-ethyl-O'-[4-(methylthio)-m-tolyl]diester ("Nemacur")
Insecticides:
3-hydroxy-N-methylcrotonamide (dimethylphosphate) ester (Azodrin ®)
methylcarbamic acid, ester with 2,3-dihydro-2,2-dimethyl-7-benzofuranol (Furadan ®)
O-[2,4,5-trichloro-α-(chloromethyl)benzyl]phosphoric acid, O',O'-dimethyl ester (Gardona ®)
2-mercaptosuccinic acid, diethyl ester, S-ester with thionophosphoric acid, dimethyl ester (Malathion ®)
phosphorothioic acid, O,O-dimethyl, O-p-nitrophenyl ester (methyl parathion)
methylcarbamic acid, ester with α-naphthol (Sevin ®)
methyl O-(methylcarbamoyl)thiolacetohydroxamate (methomyl)
O,O-diethyl-O-(2-isopropyl-4-methyl-6-pyrimidyl)phosphorothioate (Diazinon ®)
octachlorocamphene (toxaphene)
O-ethyl O-p-nitrophenyl phenylphosphonothioate (EPN)
cyano(3-phenoxyphenyl)methyl 4-chloro-α-(1-methylethyl)benzeneacetate (Pydrin ®)
(3-phenoxyphenyl)methyl(±)-cis,trans-3-(2,2-dichloroethenyl)-2,2-dimethylcyclopropanecarboxylate (Ambush ®)
O-ethyl-S-(p-chlorophenyl)ethylphosphonodithioate (Curacron ®)
phosphorothiolothionic acid, O-ethyl-O-[4-(methylthio)phenyl]-S-n-propyl ester (Bolstar ®)

The agricultural chemicals listed above are merely exemplary of compounds that may be mixed with the active compounds of this invention.

The compounds are especially suited for the protection of living plants such as fruit-bearing trees, nut-bearing trees, ornamental trees, forest trees, vegetable crops, horticultural crops (including ornamentals, small fruit and berries) and grain and seed crops. Apple trees, peach trees, cotton, citrus trees, bean and peanuts are particularly susceptible to mite damage and can be protected by application of the compounds of this inention. To assure control throughout the growing season (e.g., June through August in the Northern Hemisphere) multiple applicaions at desired intervals can be utilized.

Many species of mites are controlled by the compounds of this invention. The following is a list of representative susceptible mites along with the types of damage that they can cause: *Panonychus ulmi* (European red mite) and *Tetranychus urticae* (two-spotted mite) which are commonly called "orchard mites," and which attack a great many deciduous trees, such as apple, pear, cherry, plum and peach trees; *Tetranychus altanticus* (Atlantic or strawberry mite), *T. cinnabarinus* (carmine spider mite) and *T. pacificus* (Pacific mite); which attack cotton and numerous other crop plants; *Paratetranychus citri* (citrus red mite) and others which attack citrus; *Phyllocoptruta oleivora* which causes citrus rust; *Bryobia praetiosa* (clover mite) which attacks clover, alfalfa and other crops; and *Aceria neocynodomis* which attacks grasses and other plants.

The compounds of this invention are also useful as plant disease control agents. They are effective for the control of a broad spectrum of plant diseases as represented by but not limited to soil borne fungal pathogens *Rhizoctonia solani* and *Phytophthora parasitica*, a pathogen that infects seeds and seedlings, *Helminthosporium oryzae*, a fungus that attacks stems and leaves, *Puccinia graminis*, a fungus that causes leaf and fruit lesions, *Venturia inaequalis*, and a fruit and vegetable rotting fungus, *Sclerotinia sclerotiorum*. Diseases of a wide variety of ornamental, vegetable cereal and fruit crops are controlled by the compounds of this invention.

Disease control is accomplished by applying the compound to the portion of the plant to be protected such as the roots, stems, foliage, fruit, seeds, tubers or bulbs, or to the media (soil) in which the plants to be protected are growing.

Rates of application for these compounds will be influenced by many factors of the environment and must be determined under use conditions. Seed and seedlings can normally be protected when seed is treated at a rate of from 0.06 to about 3 grams per kilogram of seed. Plants growing in soil treated at a concentration of from 0.1 to about 20 kg/ha can be protected from disease. Compositions of this invention may contain, in addition to a compound of this invention, conventional pesticides, such as insecticides, miticides, bactericides, nematicides, fungicides or other agricultural chemicals such as growth modifying agents. Representative examples of these are listed above.

The compounds of this invention are also useful as insect ovicides. The species that may be controlled include but are not limited to beet armyworm (*Spodoptera exigua*), and southern armyworm (*Spodoptera frugiperda*), potato tuberworm (*Phthorimaea operculella*), cotton bollworm (*Heliothis zea*) and tobacco budworm (*Heliothis virescens*).

Spray applications of 0.1–2 kg per hectare to foliage containing eggs will prevent further development of the embroyos thereby protecting the plant from the feeding effect of voracious larvae. Plants to be protected include a wide range of vegetable and field crops, ornamentals and forest trees.

EXAMPLE A

Test units consisted of plant pots containing two red kidney bean plants in the two-leaf stage per pot. The plants were infested with two-spotted mites and sprayed to run-off with solutions of 1,1,1-trichloro-N-(2-chloro-5-trifluoromethylphenyl)-N-(2,4-dinitro-6-trifluoromethylphenyl)methanesulfenamide. Solutions were made by dissolving weighed quantities of the active ingredients in 10 ml. of acetone and then diluting to volume with water containing 1:3000 of a surfactant, Duponol ®. Mortality was evaluated two days after spraying.

| % Spray Concentration | % Mortality (2 Days) |
|---|---|
| .001 | 100 |
| .0005 | 99 |
| .00025 | 96 |

EXAMPLE B

Bean plants, infested with two-spotted mites, were sprayed to run-off with the indicated concentration of 1,1,1-trichloro-N-(2-chloro-5-trifluoromethoxyphenyl)-N-(2,4-dinitro-6-trifluoromethylphenyl)-methanesulfenamide 50/50 mixture with the 5-chloro-2-trifluoromethoxyphenyl isomer in Duponol ®: water at 1:3000. Mortality after two days is set forth below.

| % Spray Concentration | % Mortality (2 Days) |
|---|---|
| .001 | 100 |
| .0005 | 97 |
| .00025 | 93 |

EXAMPLE C

*Rhizoctonia solani* infested soil was placed in a 900 cc cup. 1,1,1-Trichloro-N-(2-chloro-5-trifluoromethoxyphenyl)-N-(2,4-dinitro-6-trifluoromethylphenyl)methanesulfenamide 50/50 mixture with the 5-chloro-2-trifluoromethoxyphenyl isomer was mixed in a section 2" wide×2" deep×4" long to simulate an in-the-row application. Five cotton seeds were planted in the treated soil. After 8 days, the cotton plants were removed and rated for disease control.

| kg/ha 40" row | Percent *Rhizoctonia solani* Control |
|---|---|
| 1.5 | 100 |
| 0.5 | 100 |
| Untreated Control | 0 |

EXAMPLE D

Portion of soil infested with *Phytophthora parasitica* were treated by mixing with various concentrations of 1,1,1-trichloro-N-[2-chloro-5-(trifluoromethyl)phenyl]-N-[2,4-dinitro-6-(trifluoromethyl)phenyl]-methanesulfenamide. These treated portions of infested soil and also portions left untreated were placed in pots and planted with tobacco seeldings about 5 cm tall. After four weeks, all of the tobacco seedlings in the untreated soil were dead with symptoms of the black shank disease. On the other hand, those seedlings planted in soil treated with 20 or 10 or 5 kg/Ha of the compound of this invention were growing well and showed no disease symptoms.

EXAMPLE E

Surface sterilized carrot sections were dipped 5 minutes in a solution containing 100 ppm of the 1,1,1-trichloro-N-(2-chloro-5-trifluoromethylphenyl)-N-(2,4-dinitro-6-trifluoromethylphenyl)methanesulfenamide. Additional sections were dipped in a check solution which contained 500 ppm Trem ® 014, 5 ml acetone and 30 ml of sterilized water.

After inoculation by placing a mycelial plug of *Sclerotinia sclerotiorum* on each carrot section, the test was held at 20° for six days.

The untreated carrot sections were completely invaded with the mycelial growth of the white mold fungus but the treated sections were totally free of growth by this disease causing organism.

EXAMPLE F 1,1,1-trichloro-N-(2-chloro-5-trifluoromethoxyphenyl)-N-(2,4-dinitro-6-trifluoromethylphenyl)-methanesulfenamide 50/50 mixtures with the 5-chloro-2-trifluoromethoxyphenyl isomer was dissolved in acetone in an amount equal to 10% of the final volume and then suspended at concentrations of 16, 3, and 1.6 ppm in purified water containing 250 ppm of the sufractant Trem ® 014 (polyhydric alcohol esters). This suspension was sprayed to the point of run-off on wheat seedlings.

The following day the wheat seedlings were inocculated with a spore suspension of the fungus *Puccinia graminis* var. tritici and incubated in a saturated humidity chamber at 20° for 24 hours, and then in a plant growth chamber for an additional 7 days when disease ratings were made. The plants treated with the compound of this invention were free of leaf infection (100% control) in contrast to the untreated plants which were covered with rust pustules. No injury was noted on treated wheat.

EXAMPLE G 1,1,1-Trichloro-N-(2-chloro-5-trifluoromethylphenyl)-N-(2,4-dinitro-6-trifluoromethylphenyl)methanesulfenamide was dissolved in acetone in an amount equal to 10% of the final volume and then suspended at a concentration of 16 ppm in purified water containing 250 ppm of the surfactant Trem ® 014 (polyhydric alcohol esters). This suspension was sprayed to the point of run-off on young apple seedlings in a vigorous state of growth. The following day, the apple seedlings were inoculated with a spore suspension of the fungus *Venturia inaequalis* and incubated in a saturated humidity chamber at 20° for 24 hours, and then in a plant growth chamber for an additional 10 days when disease and plant injury ratings were made. The plants treated with the compound of this invention were free of leaf infection (100% control) in contrast to the untreated plants which were covered with scab lesions.

EXAMPLE H 1,1,1-Trichloro-N-(2-chloro-5-trifluoromethylphenyl)-N-(2,4-dinitro-6-trifluoromethylphenyl)methanesulfenamide was dissolved in acetone base solvent and applied to rice seed infected with *Helminthosporium oryzae*. Treated seeds were allowed to dry, then planted. In Test 1 treated seed was placed directly on moist blotting paper, covered with polyethylene covers and allowed to germinate and grow at 21°. This test was rated 2 weeks following planting.

In Test 2 treated seed was planted in cups of sterile soil and allowed to germinate and grow in the greenhouse. Soil was kept moist. In this test, treatments were replicated 5 times. The test was evaluated 10 days following planting.

In both tests:
1. Disease control was determined on the basis of healthy plants.
2. Crop phytotoxicity was shown as crop growth reduction and rated on a 0–10 scale with 0 being no phytotoxicity and 10 being no growth.

The following are the results of two rice tests:

| Test # | Rate, g ai/kg | % Healthy Plants | Crop Growth Reduction |
|---|---|---|---|
| 1 | 0.06 | 90 | 0 |
|   | 0.6 | 80 | 2 |
|   | 1.3 | 60 | 5 |
|   | 2.5 | 50 | 5 |
| 2 | 0.075 | 58 | 2 |
|   | 0.15 | 64 | 2 |
|   | 0.30 | 74 | 1 |
|   | 0.60 | 82 | 1 |
| Untreated Check | — | 56 | 3 |

EXAMPLE I

Eggs of the potato tuberworm, *Phthorimaea operculella*, were laid on muslin cloth. Discs, each containing 50–75 eggs, were dipped for 10 seconds in the indicated concentration of 1,1,1-trichloro-N-(2-chloro-5-trifluoromethoxyphenyl)-N-(2,4-dinitro-6-trifluoromethylphenyl)methanesulfenamide extended in Dupanol®:water at 1:3000. The discs were then placed in petri dishes for three days. Percent control (% eggs failed to hatch) is summarized below.

| % Concentration | % Control (3 Days) |
|---|---|
| .03 | 100 |
| .01 | 100 |
| Untreated Check | 9 |

EXAMPLE J

Eggs of the beet armyworm, *Spodoptera exigua*, were laid on cellophane. Discs, each containing 50–75 eggs, were placed in petri dishes and lightly sprayed with the indicated concentration of 1,1,1-trichloro-N-(2-chloro-5-trifluoromethylphenyl)-N-(2,4-dinitro-6-trifluoromethylphenyl)methanesulfenamide in acetone solution. Three days later, percent control (% eggs failing to hatch) was determined.

| % Concentration | % Control (3 days) |
|---|---|
| 0.05 | 100 |
| 0.005 | 50 |
| Untreated Check | 0 |

What is claimed is:
1. A compound of the formula

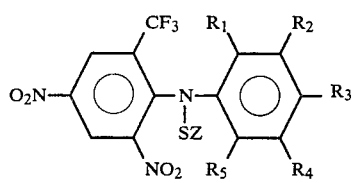

wherein
$R_1$, $R_3$ and $R_4$ independently are H, F, Cl, Br, $NO_2$, $CF_3$, $OCF_3$ or $OCF_2CF_2H$;
$R_2$ is H, F, Cl, Br, $NO_2$ and $CF_3$;
$R_5$ is H or F;
Z is $CCl_3$, $CCl_2F$, $CCl_2CCl_2H$ or $CCl_2CFCl_2$;
provided that when $R_1$ is $NO_2$ or $CF_3$, then $R_3$ must be H or F;
provided that no more than two of the substituents $R_1$, $R_2$, $R_3$ and $R_4$ are simultaneously Cl, Br, $NO_2$, $CF_3$, $OCF_3$ or $OCF_2CF_2H$ and when two $NO_2$ groups are present, they are not ortho to each other.

2. A compound of claim 1 wherein Z is $CCl_3$.
3. A compound of claim 1 wherein $R_1$ is F, Cl, Br, $CF_3$, $OCF_3$ or $OCF_2CF_2H$.
4. A compound of claim 1 where $R_2$ is H, F, Cl or Br.
5. A compound of claim 1 where $R_3$ is H, F, Cl or Br.
6. A compound of claim 1 where $R_4$ is F, Cl, Br, $CF_3$, $OCF_3$ or $OCF_2CF_2H$.
7. A compound of claim 1 where
Z is $CCl_3$;
$R_1$ and $R_4$ independently are Cl, $CF_3$, $OCF_3$ or $OCF_2CF_2H$; and
$R_2$, $R_3$ and $R_5$ are H.
8. The compound of claim 1 which is 1,1,1-trichloro-N-[2-chloro-5-(trifluoromethyl)phenyl]-N-[2,4-dinitro-6-(trifluoromethyl)phenyl]methanesulfenamide.
9. A composition containing at least two compounds of the formula of claim 1.
10. A composition of claim 9 where the compounds are 1,1,1-trichloro-N-[2-chloro-5-(trifluoromethoxy)phenyl]-N-[2,4-dinitro-6-(trifluoromethyl)phenyl]methanesulfenamide and 1,1,1-trichloro-N-[5-chloro-2-(trifluoromethoxy)phenyl]-N-[2,4-dinitro-6-(trifluoromethyl)]methanesulfenamide.
11. An miticidal fungicidal or ovicidal composition comprising a diluent, surfactant or mixtures thereof and a miticidally, fungicidally or ovicidally effective amount of a compound of claim 1.
12. An miticidal, fungicidal, or ovicidal composition comprising a diluent, surfactant or mixtures thereof and a miticidally, fungicidally or ovicidally effective amount of a compound of claim 2.
13. An miticidal, fungicidal, or ovicidal composition comprising a diluent, surfactant or mixtures thereof and a miticidally, fungicidally or ovicidally effective amount of a compound of claim 3.
14. An miticidal or ovicidal composition comprising a diluent, surfactant or mixtures thereof and a miticidally, fungicidally or ovicidally effective amount of a compound of claim 4.
15. An miticidal, fungicidal or ovicidal composition comprising a diluent, surfactant or mixtures thereof and a miticidally, fungicidally or ovicidally effective amount of a compound of claim 5.
16. A miticidal, fungicidal or ovicidal composition comprising a diluent, surfactant or mixtures thereof and a miticidally, fungicidally or ovicidally effective amount of a compound of claim 6.
17. An miticidal, fungicidal or ovicidal composition comprising a diluent, surfactant or mixtures thereof and a miticidally, fungicidally or ovicidally effective amount of a compound of claim 7.
18. An miticidal, fungicidal or ovicidal composition comprising a diluent, surfactant or mixtures thereof and a miticidally, fungicidally or ovicidally effective amount of a compound of claim 8.

19. An miticidal, fungicidal or ovicidal composition comprising a diluent, surfactant or mixtures thereof and a miticidally, fungicidally or ovicidally effective amount of a composition of claim 9.

20. An miticidal, fungicidal or ovicidal composition comprising a diluent, surfactant or mixtures thereof and a miticidally, fungicidally or ovicidally effective amount of a composition of claim 10.

21. A method for control of mites, fungus disease of a plant or insect eggs which comprises applying to a locus to be protected a miticidally, fungicidally or ovicidally effective amount of a compound of claim 1.

22. A method for control of mites, fungus disease of a plant or insect eggs which comprises applying to a locus to be protected a miticidally, fungicidally or ovicidally effective amount of a compound of claim 2.

23. A method for control of mites, fungus disease of a plant or insect eggs which comprises applying to a locus to be protected a miticidally, fungicidally or ovicidally effective amount of a compound of claim 3.

24. A method for control of mites, fungus disease of a plant or insect eggs which comprises applying to a locus to be protected a miticidally, fungicidally or ovicidally effective amount of a compound of claim 4.

25. A method for control of mites, fungus disease of a plant or insect eggs which comprises applying to a locus to be protected a miticidally, fungicidally or ovicidally effective amount of a compound of claim 5.

26. A method for control of mites, fungus disease of a plant or insect eggs which comprises applying to a locus to be protected a miticidally, fungicidally or ovicidally effective amount of a compound of claim 6.

27. A method for control of mites, fungus disease of a plant or insect eggs which comprises applying to a locus to be protected a miticidally, fungicidally or ovicidally effective amount of a compound of claim 7.

28. A method for control of mites, fungus disease of a plant or insect eggs which comprises applying to a locus to be protected a miticidally, fungicidally or ovicidally effective amount of a compound of claim 8.

29. A method for control of mites, fungus disease of a plant or insect eggs which comprises applying to a locus to be protected a miticidally, fungicidally or ovicidally effective amount of a compound of claim 9.

30. A method for control of mites, fungus disease of a plant of insect eggs which conprises applying to a locus to be protected a miticidally, fungicidally or ovicidally effective amount of a compound of claim 10.

31. A method for control of mites which comprises applying to the locus to be protected a miticidally effective amount of a compound of claim 1.

32. A method for control of mites which comprises applying to the locus to be protected a miticidally effective amount of a compound of claim 2.

33. A method for control of mites which comprises applying to the locus to be protected a miticidally effective amount of a compound of claim 3.

34. A method for control of mites which comprises applying to the locus to be protected a miticidally effective amount of a compound of claim 4.

35. A method for control of mites which comprises applying to the locus to be protected a miticidally effective amount of a compound of claim 5.

36. A method for control of mites which comprises applying to the locus to be protected a miticidally effective amount of a compound of claim 6.

37. A method for control of mites which comprises applying to the locus to be protected a miticidally effective amount of a compound of claim 7.

38. A method for control of mites which comprises applying to the locus to be protected a miticidally effective amount of a compound of claim 8.

39. A method for control of mites which comprises applying to the locus to be protected a miticidally effective amount of a composition of claim 9.

40. A method for control of mites which comprises applying to the locus to be protected a miticidally effective amount of a composition of claim 10.

41. A method for control of fungus disease of a plant which comprises applying to a locus to be protected a fungicidally effective amount of a compound of claim 1.

42. A method for control of fungus disease of a plant which comprises applying to a locus to be protected a fungicidally effective amount of a compound of claim 2.

43. A method for control of fungus disease of a plant which comprises applying to a locus to be protected a fungicidally effective amount of a compound of claim 3.

44. A method for control of fungus disease of a plant which comprises applying to a locus to be protected a fungicidally effective amount of a compound of claim 4.

45. A method for control of fungus disease of a plant which comprises applying to a locus to be protected a fungicidally effective amount of a compound of claim 5.

46. A method for control of fungus disease of a plant which comprises applying to a locus to be protected a fungicidally effective amount of a compound of claim 6.

47. A method for control of fungus disease of a plant which comprises applying to a locus to be protected a fungicidally effective amount of a compound of claim 7.

48. A method for control of fungus disease of a plant which comprises applying to a locus to be protected a fungicidally effective amount of a compound of claim 8.

49. A method for control of fungus disease of a plant which comprises applying to a locus to be proteced a fungicidally effective amount of a composition of claim 9.

50. A method for control of fungus disease of a plant which comprises applying to a locus to be proteced a fungicidally effective amount of a composition of claim 10.

* * * * *